United States Patent [19]

Winklemann et al.

[11] Patent Number: 4,593,027
[45] Date of Patent: Jun. 3, 1986

[54] 3-ARYL-7-CHLORO-3,4-DIHYDROACRIDINE-1,9(2H,10H)-DIONE 1-OXIMES AND 1-HYDRAZONE DERIVATIVES, THEIR SALTS, A PROCESS FOR THEIR PREPARATION, AGENTS CONTAINING THEM AND THEIR USE

[75] Inventors: Erhardt Winklemann, Kelkheim; Walter Dürckheimer, Hattersheim am Main; Wolfgang Raether, Dreieich, all of Fed. Rep. of Germany

[73] Assignee: Hoechst Aktiengesellschaft, Fed. Rep. of Germany

[21] Appl. No.: 540,647

[22] Filed: Oct. 11, 1983

[30] Foreign Application Priority Data

Oct. 11, 1982 [DE] Fed. Rep. of Germany ....... 3237649
Dec. 24, 1982 [DE] Fed. Rep. of Germany ....... 3247908

[51] Int. Cl.[4] .................. A61K 31/495; A61K 31/435; C07D 295/04; C07D 471/00
[52] U.S. Cl. ..................................... 514/253; 514/297; 544/59; 544/162; 544/361; 544/363; 544/392; 546/103; 564/19; 564/36; 564/250
[58] Field of Search ................ 544/361, 363; 424/250; 514/253, 254

[56] References Cited

U.S. PATENT DOCUMENTS

| | | | |
|---|---|---|---|
| 2,880,210 | 3/1959 | Elslager et al. | 544/363 |
| 3,126,384 | 3/1964 | Gaillot et al. | 544/363 |
| 3,184,452 | 5/1965 | Druey et al. | 544/361 |
| 3,577,558 | 5/1971 | Rosi | 424/250 |
| 3,712,943 | 1/1973 | Mayer et al. | 546/106 |
| 3,947,449 | 5/1976 | Dürckheimer et al. | 546/103 |
| 4,178,451 | 12/1979 | Wade et al. | 424/250 |
| 4,235,899 | 11/1980 | Gebert et al. | 424/250 |
| 4,260,615 | 4/1981 | Raether et al. | 546/103 |
| 4,266,062 | 5/1981 | Rasmussen | 544/363 |
| 4,291,034 | 9/1981 | Werbel | 424/250 |
| 4,440,771 | 4/1984 | Scovill et al. | 544/363 |
| 4,447,427 | 5/1984 | Klayman et al. | 424/250 |

FOREIGN PATENT DOCUMENTS 0036718 3/1981 European Pat. Off. .

OTHER PUBLICATIONS

Merck & Co., The Merck Index, 9th ed., (1976), pp. 970–971.
Konopa et al. Neoplasma 16, 2, 1969, pp. 171–179, "in vitro Studies on the Cytotoxic Properties of 9-Amino-Nitroacridine Derivatives".
Duerckheimer et al., Chemical Abstracts vol. 93, 220561u (1980).
Raether & Mehlhorn, Chemical Abstracts, vol. 101(7):48222e (1984).

Primary Examiner—Donald G. Daus
Assistant Examiner—Stephen N. Kapner
Attorney, Agent, or Firm—Finnegan, Henderson, Farabow, Garrett & Dunner

[57] ABSTRACT

3-Aryl-7-chloro-3,4-dihydroacridine-1,9(2H,10H)-dione 1-oximes and 1-hydrazone derivatives of the formula I and their physiologically tolerated acid addition and ammonium salts are described, as is a process for their preparation. The new compounds are chemotherapeutic agents and are active against protozoa, especially malaria plasmodia.

8 Claims, No Drawings

3-ARYL-7-CHLORO-3,4-DIHYDROACRIDINE-1,9(2H,10H)-DIONE 1-OXIMES AND 1-HYDRAZONE DERIVATIVES, THEIR SALTS, A PROCESS FOR THEIR PREPARATION, AGENTS CONTAINING THEM AND THEIR USE

3-Aryl-7-chloro-10-hydroxy-3,4-dihydroacridine-1,9(2H,10H)-diones which are suitable for combating protozoa, especially plasmodia (malaria) and coccidia, are described in German Pat. No. 2,337,474 corresponding to U.S. Pat. No. 3,947,449. 3-Aryl-7-chloro-10-hydroxy-3,4-dihydroacridine-1,9(2H,10H)-dione 1-imines which are also effective against protozoa are described in the European Patent Application having the publication number 36,718 corresponding to U.S. Pat. No. 4,291,034.

The invention relates to 3-aryl-7-chloro-3,4-dihydroacridine-1,9(2H,10H)-dione 1-oximes and 1-hydrazone derivatives of the formula I

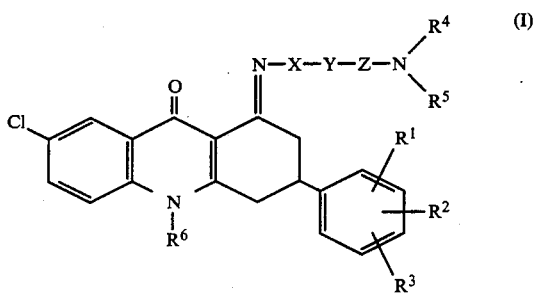

and their physiologically tolerated acid addition and ammonium salts.

In the formula, $R^1$, $R^2$ and $R^3$ denote hydrogen, halogen, especially fluorine, chlorine or bromine, $C_1$-$C_4$-alkyl, especially methyl, trifluoromethyl, $C_1$-$C_4$-alkoxy, especially methoxy, trifluoromethoxy, difluorochloromethoxy, 1,1,2,2-tetrafluoroethoxy, phenoxy, halogenophenoxy, especially chlorophenoxy, $C_1$-$C_4$-alkylthio, phenylthio and naphthylthio, especially methylthio and phenylthio, $C_1$-$C_4$-alkylsulfinyl, phenylsulfinyl and naphthylsulfinyl, especially methylsulfinyl and phenylsulfinyl, $C_1$-$C_4$-alkylsulfonyl, phenylsulfonyl and naphthylsulfonyl, especially methylsulfonyl and phenylsulfonyl, trifluoromethylthio, carbamyl, sulfamyl, cyano or nitro, $R^1$, $R^2$ and $R^3$ being identical or different (a) X denotes oxygen, Y denotes a single bond and Z denotes a straight-chain or branched alkylene chain having 2 to 5 carbon atoms which is optionally substituted by a hydroxyl group, (b) X, Y and Z denote a single bond, (c) X denotes the —NR— group, in which R denotes hydrogen or $C_1$-$C_4$-alkyl, Y denotes a single bond and Z denotes a straight-chain or branched alkylene chain having 2 to 5 carbon atoms, (d) X denotes the —NR— group, in which R denotes hydrogen or $C_1$-$C_4$-alkyl, Y denotes the carbonyl, thiocarbonyl or iminocarbonyl group and Z denotes a single bond, (e) X denotes the —NR— group, in which R denotes hydrogen or $C_1$-$C_4$-alkyl, Y denotes the carboxamido, thiocarboxamido or carboxamidino group and Z denotes a straight-chain or branched alkylene chain having 2 to 5 carbon atoms, (f) X denotes the —NR— group, in which R denotes hydrogen or $C_1$-$C_4$-alkyl, Y denotes the carbonyl group and Z denotes a straight-chain or branched alkylene chain having 1 to 3 carbon atoms, (g) X denotes the —NR— group, in which R denotes hydrogen or $C_1$-$C_4$-alkyl, Y denotes the carboxyl group and Z denotes a straight-chain or branched alkylene chain having 2 to 5 carbon atoms, $R^4$ and $R^5$ denote hydrogen or straight-chain or branched $C_1$-$C_4$-alkyl, such as methyl, ethyl, propyl, isopropyl, butyl or isobutyl, $R^4$ and $R^5$ being identical or different, or $R^4$ and $R^5$ together denote an alkylene chain having 4 to 6 carbon atoms which form, with the nitrogen atom, a 5- to 7-membered heterocyclic ring, in which it is possible for one —$CH_2$-group to be replaced by another heteroatom from the group comprising nitrogen, oxygen or sulfur, and it being possible for the heterocyclic ring in turn to be substituted by an alkyl group which is optionally substituted by a hydroxyl group and has one to three carbon atoms, such as methyl, ethyl, 2-hydroxyethyl or propyl, or by phenyl-$C_1$-$C_3$-alkyl or naphthyl-$C_1$-$C_3$-alkyl, such as benzyl, or by phenyl or naphthyl which is optionally substituted by methyl, methoxy, chlorine or trifluoromethyl, such as phenyl, tolyl, methoxyphenyl, chlorophenyl or trifluoromethylphenyl, especially pyrrolidino, 2-methylpyrrolidino, 2,5-dimethylpyrrolidino, piperidino, 2-methylpiperidino, 4-methylpiperidino, 2,6-dimethylmorpholino, morpholino, thiomorpholino, piperazino, N-methylpiperazino, N-ethylpiperazino, N-benzylpiperazino, N-phenylpiperazino, N-4-tolylpiperazino, N-4-methoxyphenylpiperazino, N-4-chlorophenylpiperazino or N-3-trifluoromethylphenylpiperazino, and $R^6$ denotes hydrogen or the hydroxyl group.

Depending on the definition of the linkage X-Y-Z, the substituents in the 1-position of the 3-aryl-7-chloro-10-hydroxy-3,4-dihydroacridine-1,9(2H,10H)-dione 1-oximes and 1-hydrazone derivatives according to the invention have the following formulae:

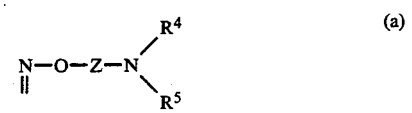

(a)

(b)

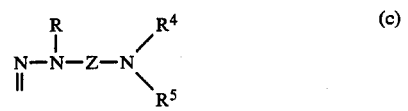

(c)

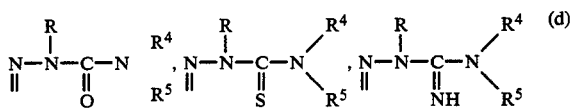

(d)

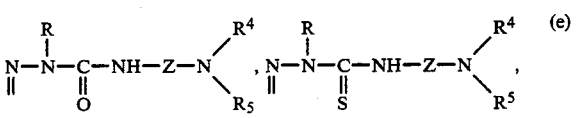

(e)

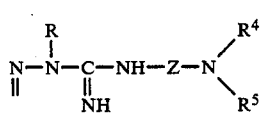

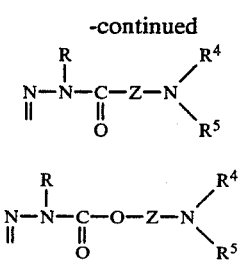

Those compounds of the formula I in which $R^1$ and $R^2$ denote hydrogen, $R^3$ denotes chlorine or trifluoromethyl, X, Y and Z denote a single bond, and $R^4$ and $R^5$, together with the nitrogen atom, denote a piperazine ring which is optionally substituted on the nitrogen are preferred. Those compounds in which the substituent $R^3$ is in the 4-position are quite especially preferred.

The invention likewise relates to a process for the preparation of 3-aryl-7-chloro-3,4-dihydroacridine-1,9(2H,10H)-dione 1-oximes and 1-hydrazone derivatives of the formula I and their salts, which comprises reacting a 3-aryl-7-chloro-3,4-dihydroacridine-1,9(2H,10H)-dione of the formula II

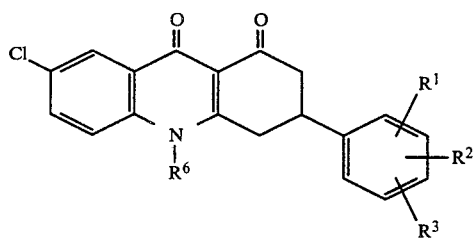

in which $R^1$, $R^2$, $R^3$ and $R^6$ have the indicated meanings, with a compound of the formula III

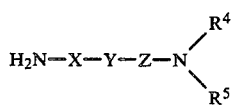

in which X, Y, Z and $R^4$ and $R^5$ have the indicated meanings, or their salts, and converting the reaction product, where appropriate, with a physiologically tolerated acid into the corresponding acid addition salt or with an alkylating agent into the corresponding ammonium salt.

The starting materials of the formula II are either known (cf. for example German Pat. No. 2,337,474 corresponding to U.S. Pat. No. 3,947,449 and Arzneimittelforschung, Drug Research, 30 (II), No. 7, pages 1041–46 (1980)) or are prepared in a manner analogous to that described in German Pat. No. 2,337,474 corresponding to U.S. Pat. No. 3,947,499 by reaction (reduction) of 3-aryl-7-chloro-10-hydroxy-3,4-dihydroacridine-1,9(2H,10H)-diones with phosphorus trihalides (phosphorus trichloride) or by reaction of 5-chloroanthranilic acid or its derivatives, such as, for example, esters or anhydrides, with 5-aryl-1,3-cyclohexanediones.

Likewise, the starting materials of the formula III are either known or are prepared by known methods which are described in the specialist literature (cf. for example Houben-Weyl, Methoden der Organischen Chemie (Methods of Organic Chemistry), Georg Thieme Verlag, Stuttgart).

Examples of suitable starting materials of the formula II are the following: 3-(2-, 3- or 4-fluoro)-phenyl, 3-(2-, 3- or 4-chloro)phenyl-, 3-(2-, 3- or 4-bromo)phenyl-, 3-(2-, 3- or 4-iodo)phenyl-, 3-(2,4-, 3,4-, 2,5- or 2,6-dichloro)phenyl-, 3-(2-fluoro-4-chloro)-phenyl-, 3-phenyl-, 3-(2-, 3- or 4-methyl)-phenyl-, 3-(2-methyl-4-chloro)phenyl-, 3-(3-methyl-4-chloro)phenyl-, 3-(2-, 3- or 4-trifluoromethyl)phenyl-, 3-(3,5-bistrifluoromethyl)phenyl-, 3-(2-chloro-4-trifluoromethyl)-phenyl-, 3-(2-, 3- or 4-methoxy)phenyl-, 3-(3,4- or 3,5-dimethoxy)phenyl-, 3-(2-chloro-4-methoxy)phenyl-, 3-(2-, 3- or 4-trifluoromethoxy)phenyl-, 3-(2-, 3- or 4-difluorochloromethoxy)phenyl-, 3-(2-, 3- or 4-(1,1,2,2-tetrafluoroethoxy))phenyl-, 3-(2-, 3- or 4-phenoxy)-phenyl-, 3-(2-, 3- or 4-(4-chlorophenoxy))phenyl-, 3-(2-, 3- or 4-methylthio)phenyl-, 3-(2-, 3- or 4-phenylthio)-phenyl-, 3-(2-, 3- or 4-methylsulfinyl)phenyl-, 3-(2-, 3- or 4l-methylsulfonyl)phenyl-, 3-(2-, 3- or 4-phenylsulfinyl)phenyl-, 3-(2-, 3- or 4-phenylsulfonyl)-phenyl-, 3-(2-, 3- or 4-trifluoromethylthio)phenyl-, 3-(2-, 3- or 4-carbamyl)phenyl-, 3-(2-, 3- or 4-sulfamyl)phenyl-, 3-(2-, 3- or 4-cyano)phenyl-, 3-(2-, 3- or 4-nitro)phenyl-, -7-chloro-10-hydroxy-3,4-dihydroacridine-1,9(2H,10H)-dione or -7-chloro-3,4-dihydroacridine-1,9(2H,10H)-dione.

Examples of suitable starting materials of the formula III are the following:

(a) O-(2-Aminoethyl, 2-aminopropyl, 3-aminopropyl or 4-aminobutyl)-, O-(2-N-methylaminoethyl, 2-N-methylaminopropyl, 3-N-methylaminopropyl or 4-N-methylaminobutyl)-, O-(2-N-ethylaminoethyl, 2-N-ethylaminopropyl, 3-N-ethylaminopropyl or 4-N-ethylaminobutyl)-, O-(2-N-n-propylaminoethyl, 2-N-n-propylaminopropyl, 3-N-n-propylaminopropyl or 4-N-n-propylaminobutyl)-, O-(2-N-n-butylaminoethyl, 2-N-n-butylaminopropyl, 3-N-n-butylaminopropyl or 4-N-n-butylaminobutyl)-, O-(2-N-dimethylaminoethyl, 2-N-dimethylaminopropyl, 3-N-dimethylaminopropyl or 4-N-dimethylaminobutyl)-, O-(2-N-diethylaminoethyl, 2-N-diethylaminopropyl, 3-N-diethylaminopropyl or 4-N-diethylaminobutyl)-, O-(2-N-di-n-propylaminoethyl, 2-N-di-n-propylaminopropyl, 3-N-di-n-propylaminopropyl or 4-N-di-n-propylaminobutyl)-, O-(2-N-di-n-butylaminoethyl, 2-N-di-n-butylaminopropyl, 3-N-di-n-butylaminopropyl or 4-N-di-n-butylaminobutyl)-, O-(2-pyrrolidinoethyl, 2-pyrrolidinopropyl, 3-pyrrolidinopropyl or 4-pyrrolidinobutyl)-, O-(2-piperidinoethyl, 2-piperidinopropyl, 3-piperidinopropyl or 4-piperidinobutyl)-, O-(2-morpholinoethyl, 2-morpholinopropyl, 3-morpholinopropyl or 4-morpholinobutyl)-, O-(2-thiomorpholinoethyl, 2-thiomorpholinopropyl, 3-thiomorpholinopropyl or 4-thiomorpholinobutyl)-, O-(2-piperazinoethyl, 2-piperazinopropyl, 3-piperazinopropyl or 4-piperazinobutyl)-, O-(2-N-methylpiperazinoethyl, 2-N-methylpiperazinopropyl, 3-N-methylpiperazinopropyl or 4-N-methylpiperazinobutyl)-, O-(2-N-ethylpiperazinoethyl, 2-N-ethylpiperazinopropyl, 3-N-ethylpiperazinopropyl or 4-N-ethylpiperazinobutyl)-, O-(2-N-benzylpiperazinoethyl, 2-N-benzylpiperazinopropyl, 3-N-benzylpiperazinopropyl or 4-N-benzylpiperazinobutyl)-, O-(2-N-phenylpiperazinoethyl, 2-N-phenylpiperazinopropyl, 3-N-phenylpiperazinopropyl or 4-N-phenylpiperazinobutyl)-hydroxylamine or O-(3-amino, 3-methylamino, 3-N-ethylamino, 3-N-n-propylamino, 3-N-n-butylamino, 3-N,N-dimethylamino, 3-N,N-diethylamino, 3-N,N-di-n-propylamino, 3-N,N-di-n-butylamino, 3-pyrrolidino, 3-piperidino, 3-morpholino, 3-thiomorpholino, 3-piperazino, 3-N'-methylpiperazino, 3-N'-ethylpiperazino or 3-N'-phenylpiperazino-2-hyroxypropyl)-hydroxylamine, (b) N-Methyl, N-ethyl, N-n-propyl, N-n-butyl, N,N-dimethyl, N,N-diethyl, N,N-di-n-propyl or N,N-di-n-butylhydrazine, N-amino-pyrrolidine, -piperidine, -morpholine, -thiomorpholine, -piperazine, -N'-methylpiperazine, -N'-ethylpiperazine, -N'-2-hydroxyethylpiperazine, -N'-benzylpiperazine, -N'-phenylpiperazine, -hexamethyleneimine or -N'-methylhomopiperazine, N-methylamino, N-ethylamino, N-n-propylamino, N-n-butylamino, N,N-dimethylamino, N,N-diethylamino, N,N-di-n-propylamino, N,N-di-n-butylamino, pyrrolidino, piperidino, morpholino, thiomorpholino, piperazino, N'-methylpiperazino, N'-ethylpiperazino, N'-benzylpiperazino or N'-phenylpiperazino-ethyl, -propyl, -isopropyl or -butyl-hydrazine, (d) Hydrazinocarbonyl, hydrazinothiocarbonyl or hydrazinocarbimido-pyrrolidine, -piperidine, -morpholine, -thiomorpholine, -piperazine, -N'-methylpiperazine, -N'-ethylpiperazine, -N'-benzylpiperazine, -N'-phenylpiperazine or -N'-2-hydroxyethylpiperazine, (e) 1-Methyl, 1-ethyl, 1-propyl, 1-butyl, 1,1-dimethyl, 1,1-diethyl, 1,1-di-n-propyl, 1,1-di-n-butyl, 1-N,N-dimethylamino, -diethylamino, -di-n-propylamino, -di-n-butylamino, 1-pyrrolidino, -piperidino, -morpholino, -thiomorpholino, -piperazino, -N-methylpiperazino, -N-ethylpiperazino, -N-benzylpiperazino, -N-phenylpiperazino-2-ethyl, -2-propyl, -3-propyl or -4-butyl-semicarbazide, -thiosemicarbazide or -aminoguanidine, (f) Amino, N-methylamino, N-ethylamino, N-n-propylamino, N-n-butylamino, N,N-dimethylamino, N,N-diethylamino, N,N-di-n-propylamino, N,N-di-n-butylamino, pyrrolidino, piperidino, morpholino, thiomorpholino, piperazino, N'-methylpiperazino, N'-ethylpiperazino, N'-2-hydroxyethylpiperazino, N'-benzylpiperazino or N'-phenylpiperazino-acetic acid, -propionic acid, -butyric acid or -isobutyric acid hydrazide, trimethyl, triethyl, tri-n-propyl or tri-n-butyl-ammonioacetic acid, -propionic acid, -butyric acid or -isobutyric acid hydrazide chloride, bromide or iodide, (g) Amino, N-methylamino, N-ethylamino, N-n-propylamino, N-n-butylamino, N,N-dimethylamino, N,N-diethylamino, N,N-di-n-propylamino, N,N-di-n-butylamino, pyrrolidino, piperidino, morpholino, thiomorpholino, piperazino, N'-methylpiperazino, N'-ethylpiperazino, N'-benzylpiperazino or N'-phenylpiperazino-ethyl, -propyl, -isopropyl or -butyl hydrazinoformate.

The reaction of the compounds of the formula II with compounds of the formula III is advantageously carried out in molar amounts. The reactions are advantageously carried out in a solvent or distributing agent. Examples of suitable solvents or distributing agents are alcohols, such as methanol, ethanol, propanol, isopropanol, butanol, methoxyethanol or ethoxyethanol, amides, such as dimethylformamide or dimethylacetamide, also dimethyl sulfoxide, halogenated hydrocarbons, such as methylene chloride, chloroform or 1,2-dichloroethane, ethers, such as 1,2-dimethoxyethane, 1,2-diethoxyethane, tetrahydrofuran or dioxane. The reaction temperatures are, for example, between 40° and 120° C., preferably between 60° and 80° C. Depending on the reactants and the temperature range, the reaction times are a few minutes to some hours.

The reaction products obtained from the reaction usually result as free bases and can, where appropriate, be converted with physiologically tolerated acids into the corresponding salts.

Examples of suitable acids for salt formation are: hydrogen halides, in particular hydrochloric acid, also sulfuric acid, nitric acid, phosphoric acid, acetic acid, propionic acid, lactic acid, tartaric acid, citric acid, oxalic acid, succinic acid, maleic acid, fumaric acid, sorbic acid, salicylic acid, methylsulfonic, phenylsulfonic or 4-tolylsulfonic acid or 1,5-naphthalenedisulfonic acid.

Where appropriate, the free bases are converted into the ammonium salts. For this purpose, the $C_1$-$C_4$-alkyl halides, such as methyl, ethyl, propyl, butyl, i-propyl chloride, bromide and iodide and the benzyl halides, are particularly suitable.

When the ammonium salts are used as the starting compounds of the formula III, then the compounds I result as the ammonium salts.

The compounds of the formula I according to the invention have valuable chemotherapeutic properties and are particularly suitable for combating infections by protozoa in humans and animals. For example, they are distinguished by a high activity against plasmodia, the organisms causing malaria. In comparison with compounds according to German Pat. No. 2,337,474 corresponding to U.S. Pat. No. 3,947,449, they have a considerably higher efficacy. This means that the same effect is achieved after administration of considerably lower doses. The activity is particularly directed against those strains of plasmodia which no longer respond to a sufficient extent to, i.e. are resistant to, conventional medicaments, such as, for example, chloroquine and other aminoquinolines. The new compounds have no cross-resistance with known agents. The claimed compounds are also effective against the causative organisms of coccidiosis of chickens, turkeys, rabbits, cattle and pigs. Thus, the invention also relates to pharmaceutical products based on the compounds according to the invention and their use as medicaments, in particular as chemotherapeutic agents. By reason of favorable physical properties, the compounds can also be used as the salts and they permit parenteral use in addition to enteral (oral) administration.

The compounds of the formula I or their salts can be administered enterally or parenterally, depending on the purpose, in doses from 0.5 to 100 mg/kg of body weight. They can also be used in combinations with other active compounds.

They can be administered in the form pf liquids, powders, tablets or capsules. For this purpose, the compounds are mixed with auxiliaries, for example with liquid or solid fillers, solvents, emulsifiers, lubricants, masking flavors, colorants and/or buffer substances which are usual in pharmaceutics. In addition, the compounds I can also be administered mixed with suitable feedstuffs. In the following examples, ° always refers to degrees centigrade.

A. PREPARATION EXAMPLES: ($R^6$=OH)

Example 1

3-(4-Trifluoromethylphenyl)-7-chloro-10-hydroxy-3,4-dihydroacridine-1,9(2H,10H)-dione 1-(N-methyl-N'-piperazinyl)imine 40.75 g (0.1 mole) of 3-(4-trifluoromethylphenyl)-7-chloro-10-hydroxy-3,4-dihydroacridine-1,9(2H,10H)- dione are suspended in 500 ml of ethanol, 11.5 g (0.1 mole) of N-methyl-N'-aminopiperazine are added and the reaction mixture is heated to reflux for 30 minutes. A clear orange-red solution forms during this. After cooling down, the ethanol is distilled out in a rotary evaporator and the solid residue is recrystallized from toluene/cyclohexane (1:1). 43 g=85% of theory of the title compound is thus obtained in the form of orange-yellow crystals of melting point 213° C.

The preparation of the starting material 3-(4-trifluoromethylphenyl)-7-chloro-10-hydroxy-3,4-dihydroacridine-1,9(2H,10H)-dione is described in German Pat. No. 2,337,474 corresponding to U.S. Pat. No. 3,947,449.

The following compounds are prepared in a manner analogous to that described in Example 1:

(a)
1. From 3-(4-trifluoromethylphenyl)-7-chloro-10-hydroxy-3,4-dihydroacridine-1,9(2H,10H)-dione=A (for preparation, cf. German Pat. No. 2,337,474) and O-(2-N,N-dimethylaminoethyl)hydroxylamine,
A-1-[O-(2-N,N-dimethylaminoethyl)oxime] of melting point 235° is obtained;
A-1-[O-(3-N,N-dimethylaminopropyl)oxime] is obtained from
A and O-(3-N,N-dimethylaminopropyl)hydroxylamine;
A-1-[O-(2-N,N-diethylaminoethyl)oxime] of melting point 197° is obtained from
A and O-(2-N,N-diethylaminoethyl)hydroxylamine;
A-1-[O-(3-N,N-diethylaminopropyl)oxime] is obtained from
A and O-(3-N,N-diethylaminopropyl)hydroxylamine;
A-1-[O-(2-pyrrolidinoethyl)oxime] of melting point 203° is obtained from
A and O-(2-pyrrolidinoethyl)hydroxylamine;
A-1-[O-(2-piperidinoethyl)oxime] of melting point 223° is obtained from
A and O-(2-piperidinoethyl)hydroxylamine;
A-1-[O-(2-morpholinoethyl)oxime] of melting point 248° is obtained from
A and O-(2-morpholinoethyl)hydroxylamine;
A-1-[O-(2-thiomorpholinoethyl)oxime] is obtained from
A and O-(2-thiomorpholinoethyl)hydroxylamine;
A-1-[O-(2-N'-methylpiperazinoethyl)oxime] is obtained from
A and O-(2-N'-methylpiperazinoethyl)hydroxylamine;
A-1-[O-(2-N'-benzylpiperazinoethyl)oxime] is obtained from
A and O-(2-N'-benzylpiperazinoethyl)hydroxylamine;
A-1-[O-(2-N'-phenylpiperazinoethyl)oxime] is obtained from
A and O-(2-N'-phenylpiperazinoethyl)hydroxylamine;
A-1-[O-(3-N,N-dimethylamino-2-hydroxypropyl)oxime] is obtained from A and O-(3-N,N-dimethylamino-2-hydroxypropyl)hydroxylamine;
A-1-[O-(3-N,N-diethylamino-2-hydroxypropyl)oxime] is obtained from
A and O-(3-N,N-diethylamino-2-hydroxypropyl)hydroxylamine;
A-1-[O-(3-morpholino-2-hydroxypropyl)oxime] is obtained from
A and O-(3-morpholino-2-hydroxypropyl)hydroxylamine; and
A-1-[O-(3-N'-methylpiperazino-2-hydroxypropyl)oxime] is obtained from
A and O-(3-N'-methylpiperazino-2-hydroxypropyl)hydroxylamine.
(a)

2. From 3-(4-chlorophenyl)-7-chloro-10-hydroxy-3,4-dihydroacridine-1,9(2H,10H)-dione=B (preparation by the method of German Pat. No. 2,337,474) and O-(2-N,N-dimethylaminoethyl)hydroxylamine, B-1-[O-(2-N,N-dimethylaminoethyl)oxime] of melting point 250° is obtained;
B-1-[O-(3-N,N-dimethylaminopropyl)oxime] is obtained from
B and O-(3-N,N-dimethylaminopropyl)hydroxylamine;
B-1-[O-(2-N,N-diethylaminoethyl)oxime] is obtained from
B and O-(2-N,N-diethylaminoethyl)hydroxylamine;
B-1-[O-(3-N,N-diethylaminopropyl)oxime] is obtained from
B and O-(3-N,N-diethylaminopropyl)hydroxylamine;
B-1-[O-(2-pyrrolidinoethyl)oxime] is obtained from
B and O-(2-pyrrolidinoethyl)hydroxylamine;
B-1-[O-(2-piperidinoethyl)oxime] is obtained from
B and O-(2-piperidinoethyl)hydroxylamine;
B-1-[O-(2-morpholinoethyl)oxime] is obtained from
B and O-(2-morpholinoethyl)hydroxylamine;
B-1-[O-(2-thiomorpholinoethyl)oxime] is obtained from
B and O-(2-thiomorpholinoethyl)hydroxylamine;
B-1-[O-(2-N'-methylpiperazinoethyl)oxime] is obtained from
B and O-(2-N'-methylpiperazinoethyl)hydroxylamine;
B-1-[O-(2-N'-benzylpiperazinoethyl)oxime] is obtained from
B and O-(2-N'-benzylpiperazinoethyl)hydroxylamine;
B-1-[O-(2-N'-phenylpiperazinoethyl)oxime] is obtained from
B and O-(2-N'-phenylpiperazinoethyl)hydroxylamine;
B-1-[O-(3-N,N-dimethylamino-2-hydroxypropyl)oxime] is obtained from
B and O-(3-N,N-dimethylamino-2-hydroxypropyl)hydroxylamine;
B-1-[O-(3-N,N-diethylamino-2-hydroxypropyl)oxime] is obtained from
B and O-(3-N,N-diethylamino-2-hydroxypropyl)hydroxylamine;
B-1-[O-(3-morpholino-2-hydroxypropyl)oxime] is obtained from
B and O-(3-morpholino-2-hydroxypropyl)hydroxylamine; and
B-1-[O-(3-N'-methylpiperazino-2-hydroxypropyl)oxime] is obtained from
B and O-(3-N'-methylpiperazino-2-hydroxypropyl)hydroxylamine.

(b)
1. From 3-(4-trifluoromethylphenyl)-7-chloro-10-hydroxy-3,4-dihydroacridine-1,9(2H,10H)-dione=A and N,N-dimethylhydrazine, A-1-N,N-dimethylhydrazone of melting point 202° is obtained;
A-1-N,N-di-n-butylhydrazone is obtained from
A and N,N-di-n-butylhydrazine;
A-1-N-pyrrolidinimine is obtained from
A and N-aminopyrrolidine;
A-1-N-morpholinimine of melting point 243° is obtained from
A and N-aminomorpholine;
A-1-N-2-hydroxyethyl-N'-piperazinimine of melting point 210° is obtained from
A and N-2-hydroxyethyl-N'-aminopiperazine;
A-1-N-benzyl-N'-piperazinimine of melting point 240° is obtained from
A and N-benzyl-N'-aminopiperazine; and
A-1-N-phenyl-N'-piperazinimine of melting point 268° is obtained from A and N-phenyl-N'-aminopiperazine.

(c)

1. A-1-(2-N,N-dimethylaminoethyl)hydrazone from A and 2-N,N-dimethylaminoethylhydrazine;
A-1-(2-N,N-diethylaminoethyl)hydrazone of melting point 180° from
A and 2-N,N-diethylaminoethylhydrazine;
A-1-(2-piperidinoethyl)hydrazone from
A and 2-piperidinoethylhydrazine; and
A-1-(2-N'-methylpiperazinoethyl)hydrazone from
A and 2-N'-methylpiperazinoethylhydrazine.

(b)

2. From 3-(4-chlorophenyl)-7-chloro-10-hydroxy-3,4-dihydroacridine-1,9(2H,10H)-dione=B and N,N-dimethylhydrazine,
B-1-N,N-dimethylhydrazone is obtained;
B-1-N,N-butylhydrazone is obtained from
B and N,N-di-n-butylhydrazine;
B-1-N-pyrrolidinimine is obtained from
B and N-aminopyrrolidine;
B-1-N-morpholinimine is obtained from
B and N-aminomorpholine;
B-1-N-methyl-N'-piperazinimine of melting point 228° is obtained from
B and N-methyl-N'-aminopiperazine;
B-1-N-2-hydroxyethyl-N'-piperazinimine of melting point 225° is obtained from
B and N-2-hydroxyethyl-N'-aminopiperazine;
B-1-N-benzyl-N'-piperazinimine is obtained from
B and N-benzyl-N'-aminopiperazine; and
B-1-N-phenyl-N'-piperazinimine is obtained from
B and N-phenyl-N'-aminopiperazine.

(c)

2. B-1-(2-N,N-Dimethylaminoethyl)hydrazone from
B and 2-N,N'-dimethylaminoethylhydrazine;
B-1-(2-N,N-diethylaminoethyl)hydrazone from
B and 2-N,N-diethylaminoethylhydrazine;
B-1-(2-piperidinoethyl)hydrazone from
B and 2-piperidinoethylhydrazine; and
B-1-(2-N'-methylpiperazinoethyl)hydrazone from
B and 2-N'-methylpiperazinoethylhydrazine.

(b)

3. From 3-phenyl-7-chloro-10-hydroxy-3,4-dihydroacridine-1,9(2H,10H)-dione=D and N-methyl-N'-aminopiperazine, D-1-N-methyl-N'-piperazinimine of melting point 118° is obtained.

4. From 3-(4-fluorophenyl)-7-chloro-10-hydroxy-3,4-dihydroacridine-1,9(2H,10H)-dione=E and N-methyl-N'-aminopiperazine, E-1-N-methyl-N'-piperazinimine of melting point 210° is obtained.

5. From 3-(2-chlorophenyl)-7-chloro-10-hydroxy-3,4-dihydroacridine-1,9(2H,10H)-dione=G and N-methyl-N'-aminopiperazine, G-1-N-methyl-N'-piperazinimine of melting point 147° is obtained.

6. From 3-(3-chlorophenyl)-7-chloro-10-hydroxy-3,4-dihydroacridine-1,9(2H,10H)-dione=L and N-methyl-N'-aminopiperazine, L-1-N-methyl-N'-piperazinimine of melting point 203° is obtained.

7. From 3-(2,4-dichlorophenyl)-7-chloro-10-hydroxy-3,4-dihydroacridine-1,9(2H,10H)-dione=M and N-methyl-N'-aminopiperazine, M-1-N-methyl-N'-piperazinimine of melting point 157° is obtained.

8. From 3-(3,4-dichlorophenyl)-7-chloro-10-hydroxy-3,4-dihydroacridine-1,9(2H,10H)-dione=Q and N-methyl-N'-aminopiperazine, Q-1-N-methyl-N'-piperazinimine of melting point 241° is obtained.

9. From 3-(2-trifluoromethylphenyl)-7-chloro-10-hydroxy-3,4-dihydroacridine-1,9(2H,10H)-dione=T and N-methyl-N'-aminopiperazine, T-1-N-methyl-N'-piperazinimine of melting point 237° is obtained.

10. From 3-(2-chloro-4-trifluoromethylphenyl)-7-chloro-10-hydroxy-3,4-dihydroacridine-1,9(2H,10H)-dione=U and N-methyl-N'-aminopiperazine, U-1-N-methyl-N'-piperazinimine of melting point 205° is obtained.

11. From 3-(4-methoxyphenyl)-7-chloro-10-hydroxy-3,4-dihydroacridine-1,9(2H,10H)-dione=V and N-methyl-N'-aminopiperazine, V-1-N-methyl-N'-piperazinimine of melting point 152° is obtained.

12. From 3-(4-nitrophenyl)-7-chloro-10-hydroxy-3,4-dihydroacridine-1,9(2H,10H)-dione=W and N-methyl-N'-aminopiperazine, W-1-N-methyl-N'-piperazinimine of melting point 217° is obtained.

(d)

1. From 3-(4-trifluoromethylphenyl)-7-chloro-10-hydroxy-3,4-dihydroacridine-1,9(2H,10H)-dione=A and aminoguanidine, A-1-guanylhydrazone HCl of melting point 222° is obtained;
A-1-(1,1-dimethyl)semicarbazone from
A and 1,1-dimethylsemicarbazide;
A-1-(1,1-dimethyl)thiosemicarbazone from
A and 1,1-dimethylthiosemicarbazide;
A-1-(1,1-dimethyl)guanylhydrazone from
A and 1,1-dimethylaminoguanidine;
A-1-(N'-methylpiperazino-N-carbonyl)hydrazone from
A and N-hydrazinocarbonyl-N'-methylpiperazine;
A-1-(N'-methylpiperazino-N-thiocarbonyl)hydrazone of melting point 238° from
A and N-hydrazinothiocarbonyl-N'-methylpiperazine;
A-1-(N'-methylpiperazino-N-carbimido)hydrazone from
A and N-hydrazinocarbimido-N'-methylpiperazine;

(e)

1. A-1-[1-(2-N,N-dimethylaminoethyl)]semicarbazone from
A and 1-(2-N,N-dimethylaminoethyl)semicarbazide;
A-1-[1-(2-N,N-diethylaminoethyl)]semicarbazone from
A and 1-(2-N,N-diethylaminoethyl)-semicarbazide;
A-1-[1-(2-N-methylpiperazinoethyl]semicarbazone from
A and 1-(2-N-methylpiperazinoethyl)semicarbazide;
A-1-[1-(2-N,N-dimethylaminoethyl)]thiosemicarbazone from
A and 1-(2-N,N-dimethylaminoethyl)thiosemicarbazide;
A-1-[1-(2-N,N-diethylaminoethyl)]thiosemicarbazone of melting point 225° from
A and 1-(2-N,N-diethylaminoethyl)thiosemicarbazide;
A-1-[1-(2-N-methylpiperazinoethyl)]thiosemicarbazone from
A and 1-(2-N-methylpiperazinoethyl)thiosemicarbazide;
A-1-[1-(2-N,N-dimethylaminoethyl)]guanylhydrazone from
A and 1-(2-N,N-dimethylaminoethyl)aminoguanidine;
A-1-[1-(2-N,N-diethylaminoethyl)]guanylhydrazone from
A and 1-(2-N,N-diethylaminoethyl)aminoguanidine; and
A-1-[1-(2-N-methylpiperazinoethyl)]guanylhydrazone from
A and 1-(2-N-methylpiperazinoethyl)aminoguanidine.

(d)

2. From 3-(4-chlorophenyl)-7-chloro-10-hydroxy-3,4-dihydroacridine-1,9(2H,10H)-dione=B and aminoguanidine, B-1-guanylhydrazone HCl of melting point 236° is obtained;
B-1-(1,1-dimethyl)semicarbazone from
B and 1,1-dimethylsemicarbazide;
B-1-(1,1-dimethyl)thiosemicarbazone from
B and 1,1-dimethylthiosemicarbazide;
B-1-(1,1-dimethyl)guanylhydrazone from
B and 1,1-dimethylaminoguanidine;
B-1-(N'-methylpiperazino-N-carbonyl)hydrazone from
B and N-hydrazinocarbonyl-N'-methylpiperazine;
B-1-(N'-methylpiperazino-N-thiocarbonyl)hydrazone from
B and N-hydrazinothiocarbonyl-N'-methylpiperazine; and
B-1-(N'-methylpiperazino-N-carbimido)hydrazone from B and N-hydrazinothiocarbimido-N'-methylpiperazine.

(e)
2. B-1-[1-(2-N,N-dimethylaminoethyl)]semicarbazone from
B and 1-(2-N,N-dimethylaminoethyl)semicarbazide;
B-1-[1-(2-N,N-diethylaminoethyl)]semicarbazone from
B and 1-(2-N,N-diethylaminoethyl)semicarbazide;
B-1-[1-(2-N-methylpiperazinoethyl)]semicarbazone from
B and 1-(2-N-methylpiperazinoethyl)semicarbazide;
B-1-[1-(2-N,N-dimethylaminoethyl)]thiosemicarbazone from
B and 1-(2-N,N-dimethylaminoethyl)thiosemicarbazide;
B-1-[1-(2-N,N-diethylaminoethyl)]thiosemicarbazone from
B and 1-(2-N,N-diethylaminoethyl)thiosemicarbazide;
B-1-[1-(2-N-methylpiperazinoethyl)]thiosemicarbazone from
B and 1-(2-N-methylpiperazinoethyl)thiosemicarbazide;
B-1-[1-(2-N,N-dimethylaminoethyl)]guanylhydrazone from
B and 1-(2-N,N-dimethylaminoethyl)aminoguanidine;
B-1-[1-(2-N,N-diethylaminoethyl)]guanylhydrazone from
B and 1-(2-N,N-diethylaminoethyl)aminoguanidine; and
B-1-[1-(2-N-methylpiperazinoethyl)]guanylhydrazone from
B and 1-(2-N-methylpiperazinoethyl)aminoguanidine.

(f)
1. From 3-(4-trifluoromethylphenyl)-7-chloro-10-hydroxy-3,4-dihydroacridine-1,9(2H,10H)-dione=A and dimethylaminoacetic acid hydrazide, A-1-(N,N-dimethylaminoacetyl)hydrazone is obtained;
A-1-(N,N-diethylaminoacetyl)hydrazone of melting point 248° is obtained from
A and N,N-diethylaminoacetic acid hydrazide;
A-1-(morpholinoacetyl)hydrazone from
A and morpholinoacetic acid hydrazide;
A-1-(N-methyl-N'-piperazinoacetyl)hydrazone from
A and N-methyl-N'-piperazinoacetic acid hydrazide;
A-1-(2-N,N-dimethylaminopropionyl)hydrazone from
A and 2-N,N-dimethylaminopropionic acid hydrazide;
A-1-(2-N,N-diethylaminopropionyl)hydrazone from
A and 2-N,N'-diethylaminopropionic acid hydrazide;
A-1-(2-morpholinopropionyl)hydrazone from
A and 2-morpholinopropionic acid hydrazide;
A-1-(2-N-methyl-N'-piperazinopropionyl)hydrazone from
A and 2-N-methyl-N'-piperazinopropionic acid hydrazide; and
A-1-(N,N,N-trimethylammonioacetyl)hydrazone chloride of melting point 244° from
A and N,N,N-trimethylammonioacetic acid hydrazide chloride.

(g)
1. From 3-(4-trifluoromethylphenyl)-7-chloro-10-hydroxy-3,4-dihydroacridine-1,9(2H,10H)-dione=A and 2-N,N-dimethylaminoethyl hydrazinoformate, A-1-(2-N,N-dimethylaminoethyloxycarbonyl)hydrazone is obtained;
A-1-(2-N,N-diethylaminoethyloxycarbonyl)hydrazone HCl of melting point 300° from
A and 2-N,N-diethylaminoethyl hydrazinoformate;
A-1-(2-morpholinoethyloxycarbonyl)hydrazone from
A and 2-morpholinoethyl hydrazinoformate; and
A-1-(2-N-methyl-N'-piperazinoethyloxycarbonyl)hydrazone from
A and 2-N-methyl-N'-piperazinoethyl hydrazinoformate.

(f)
2. From 3-(4-chlorophenyl)-7-chloro-10-hydroxy-3,4-dihydroacridine-1,9(2H,10H)-dione=B and dimethylaminoacetic acid hydrazide, B-1-(N,N-dimethylaminoacetyl)hydrazone is obtained;
B-1-(N,N-diethylaminoacetyl)hydrazone of melting point 262° from
B and N,N-diethylaminoacetic acid hydrazide;
B-1-(morpholinoacetyl)hydrazone from
B and morpholinoacetic acid hydrazide;
B-1-(N-methyl-N'-piperazinoacetyl)hydrazone from
B and N-methyl-N'-piperazinoacetic acid hydrazide;
B-1-(2-N,N-dimethylaminopropionyl)hydrazone from
B and 2-N,N-dimethylaminopropionic acid hydrazide;
B-1-(2-N,N-diethylaminopropionyl)hydrazone from
B and 2-N,N-diethylaminopropionic acid hydrazide;
B-1-(2-morpholinopropionyl)hydrazone from
B and 2-morpholinopropionic acid hydrazide;
B-1-(2-N-methyl-N'-piperazinopropionyl)hydrazone from
B and 2-N-methyl-N'-piperazinopropionic acid hydrazide; and
B-1-(N,N,N-trimethylammonioacetyl)hydrazone chloride of melting point 233° from
B and N,N,N-trimethylammonioacetic acid hydrazide chloride.

(g)
2. From 3-(4-trifluoromethylphenyl)-7-chloro-10-hydroxy-3,4-dihydroacridine-1,9(2H,10H)-dione=B and 2-N,N-dimethylaminoethyl hydrazinoformate, B-1-(2-N,N-dimethylaminoethyloxycarbonyl)hydrazone is obtained;
B-1-(2-N,N-diethylaminoethyloxycarbonyl)hydrazone from
B and 2-N,N-diethylaminoethyl hydrazinoformate;
B-1-(2-morpholinoethyloxycarbonyl)hydrazone from
B and 2-morpholinoethyl hydrazinoformate; and
B-1-(2-N-methyl-N'-piperazinoethyloxycarbonyl)hydrazone from
B and 2-N-methyl-N'-piperazinoethyl hydrazinoformate.

B. PREPARATION EXAMPLES: ($R^6$=H)

Example 1

3-(4-Trifluoromethylphenyl)-7-chloro-3,4-dihydroacridine-1,9(2H,10H)-dione
1-(N-methyl-N'-piperazinyl)imine 39.15 g (0.1 mole) of 3-(4-trifluoromethylphenyl)-7-chloro-3,4-dihydroacridine-1,9(2H,10H)-dione are suspended in 500 ml of ethanol, 11.5 g (0.1 mole) of N-methyl-N'-aminopiperazine are added and the reaction mixture is heated to reflux for 90 minutes. A clear solution is formed during this. After cooling down, the ethanol is distilled out in a rotary evaporator and the solid residue is recrystallized from toluene/cyclohexane (1:1). 44 g (=90% of theory) of the title compound are thus obtained in the form of pale yellow crystals of melting point 246° C.

The preparation of the starting material 3-(4-trifluoromethylphenyl)-7-chloro-3,4-dihydroacridine-1,9-(2H,10H)-dione of melting point 385° C. is carried out by reacting 3-(4-trifluoromethylphenyl)-7-chloro-10-hydroxy-3,4-dihydroacridine-1,9(2H,10H)-dione of melting point 330° with phosphorus trichloride in chloroform (steam bath) in analogy to the procedure given in German Pat. No. 2,337,474.

The following compounds are prepared in a manner analogous to that described in Example 1:

(a)

1. From 3-(4-trifluoromethylphenyl)-7-chloro-3,4-dihydroacridine-1,9(2H,10H)-dione=A (for preparation, cf. German Pat. No. 2,337,474) and O-(2-N,N-dimethylaminoethyl)hydroxylamine, A-1-[O-(2-N,N-dimethylaminoethyl)oxime] of melting point 270° is obtained;
A-1-[O-(3-N,N-dimethylaminopropyl)oxime] from
A and O-(3-N,N-dimethylaminopropyl)hydroxylamine;
A-1-[O-(2-N,N-diethylaminoethyl)oxime] from
A and O-(2-N,N-diethylaminoethyl)hydroxylamine;
A-1-[O-(3-N,N-diethylaminopropyl)oxime] from
A and O-(3-N,N-diethylaminopropyl)hydroxylamine;
A-1-[O-(2-pyrrolidinoethyl)oxime] from
A and O-(2-pyrrolidinoethyl)hydroxylamine;
A-1-[O-(2-piperidinoethyl)oxime] from
A and O-(2-piperidinoethyl)hydroxylamine;
A-1-[O-(2-morpholinoethyl)oxime] from
A and O-(2-morpholinoethyl)hydroxylamine;
A-1-[O-(2-thiomorpholinoethyl)oxime] from
A and O-(2-thiomorpholinoethyl)hydroxylamine;
A-1-[O-(2-N'-methylpiperazinoethyl)oxime] from
A and O-(2-N'-methylpiperazinoethyl)hydroxylamine;
A-1-[O-(2-N'-benzylpiperazinoethyl)oxime] from
A and O-(2-N'-benzylpiperazinoethyl)hydroxylamine;
A-1-[O-(2-N'-phenylpiperazinoethyl)oxime] from
A and O-(2-N'-phenylpiperazinoethyl)hydroxylamine;
A-1-[O-(3-N,N-dimethylamino-2-hydroxypropyl)oxime] from
A and O-(3-N,N-dimethylamino-2-hydroxypropyl)hydroxylamine;
A-1-[O-(3-N,N-diethylamino-2-hydroxypropyl)oxime] from
A and O-(3-N,N-diethylamino-2-hydroxypropyl)hydroxylamine;
A-1-[O-(3-morpholino-2-hydroxypropyl)oxime] from
A and O-(3-miorpholino-2-hydroxypropyl)hydroxylamine; and
A-1-[O-(3-N'-methylpiperazino-2-hydroxypropyl)oxime] from
A and O-(3-N'-methylpiperazino-2-hydroxypropyl)hydroxylamine.

(a)

2. From 3-(4-chlorophenyl)-7-chloro-3,4-dihydroacridine-1,9(2H,10H)-dione=B (preparation by the method of German Pat. No. 2,337,474) and O-(2-N,N-dimethylaminoethyl)hydroxylamine, B-1-[O-(2-N,N-dimethylaminoethyl)oxime] of melting point 287° is obtained;
B-1-[O-(3-N,N-dimethylaminopropyl)oxime] from
B and O-(3-N,N-dimethylaminopropyl)hydroxylamine;
B-1-[O-(2-N,N-diethylaminoethyl)oxime] from
B and O-(2-N,N-diethylaminoethyl)hydroxylamine;
B-1-[O-(3-N,N-diethylaminopropyl)oxime] from
B and O-(3-N,N-diethylaminopropyl)hydroxylamine;
B-1-[O-(2-pyrrolidinoethyl)oxime] from
B and O-(2-pyrrolidinoethyl)hydroxylamine;
B-1-[O-(2-piperidinoethyl)oxime] from
B and O-(2-piperidinoethyl)hydroxylamine;
B-1-[O-(2-morpholinoethyl)oxime] from
B and O-(2-morpholinoethyl)hydroxylamine;
B-1-[O-(2-thiomorpholinoethyl)oxime] from
B and O-(2-thiomorpholinoethyl)hydroxylamine;
B-1-[O-(2-N'-methylpiperazinoethyl)oxime] from
B and O-(2-N'-methylpiperazinoethyl)hydroxylamine;
B-1-[O-(2-N'-benzylpiperazinoethyl)oxime] from
B and O-(2-N'-benzylpiperazinoethyl)hydroxylamine;
B-1-[O-(2-N'-phenylpiperazinoethyl)oxime] from
B and O-(2-N'-phenylpiperazinoethyl)hydroxylamine;
B-1-[O-(3-N,N-dimethylamino-2-hydroxypropyl)oxime] from
B and O-(3-N,N-dimethylamino-2-hydroxypropyl)hydroxylamine;
B-1-[O-(3-N,N-diethylamino-2-hydroxypropyl)oxime] from
B and O-(3-N,N-diethylamino-2-hydroxypropyl)hydroxylamine;
B-1-[O-(3-morpholino-2-hydroxypropyl)oxime] from
B and O-(3-morpholino-2-hydroxypropyl)hydroxylamine; and
B-1-[O-(3-N'-methylpiperazino-2-hydroxypropyl)oxime] from
B and O-(3-N'-methylpiperazino-2-hydroxypropyl)hydroxylamine.

(b)

1. From 3-(4-trifluoromethylphenyl)-7-chloro-3,4-dihydroacridine-1,9(2H,10H)-dione=A and N,N-dimethylhydrazine, A-1-N,N-dimethylhydrazone of melting point 240° is obtained;
A-1-N,N-di-n-butylhydrazone from
A and N,N-di-n-butylhydrazine;
A-1-N-pyrrolidinimine from
A and N-aminopyrrolidine;
A-1-N-morpholinimine from
A and N-aminomorpholine;
A-1-N-2-hydroxyethyl-N'-piperazinimine of melting point 245° from
A and N-2-hydroxyethyl-N'-aminopiperazine;
A-1-N-benzyl-N'-piperazinimine from
A and N-benzyl-N'-aminopiperazine; and
A-1-N-phenyl-N'-piperazinimine from
A and N-phenyl-N'-aminopiperazine.

(c)

1. A-1-(2-N,N-dimethylaminoethyl)hydrazone from
A and 2-N,N-dimethylaminoethylhydrazine;
A-1-(2-N,N-diethylaminoethyl)hydrazone of melting point 217° from
A and 2-N,N-diethylaminoethylhydrazine;

A-1-(2-piperidinoethyl)hydrazone from
A and 2-piperidinoethylhydrazine; and
A-1-(2-N'-methylpiperazinoethyl)hydrazone from
A and 2-N'-methylpiperazinoethylhydrazine.

(b)

2. From 3-(4-chlorophenyl)-7-chloro-3,4-dihydroacridine-1,9(2H,10H)-dione=B and N,N-dimethylhydrazine, B-1-N,N-dimethylhydrazone is obtained;
B-1-N,N-di-n-butylhydrazone from
B and N,N-di-n-butylhydrazine;
B-1-N-pyrrolidinimine from
B and N-aminopyrrolidine;
B-1-N-morpholinimine from
B and N-aminomorpholine;
B-1-N-methyl-N'-piperazinimine of melting point 270° from
B and N-methyl-N'-aminopiperazine;
B-1-N-2-hydroxyethyl-N'-piperazinimine of melting point 190° from
B and N-2-hydroxyethyl-N'-aminopiperazine;
B-1-N-benzyl-N'-piperazinimine from
B and N-benzyl-N'-aminopiperazine; and
B-1-N-phenyl-N'-piperazinimine from
B and N-phenyl-N'-aminopiperazine.

(c)

2. B-1-(2-N,N-dimethylaminoethyl)hydrazone from
B and 2-N,N-dimethylaminoethylhydrazine;
B-1-(2-N,N-diethylaminoethyl)hydrazone from
B and 2-N,N-diethylaminoethylhydrazine;
B-1-(2-piperidinoethyl)hydrazone from
B and 2-piperidinoethylhydrazine; and
B-1-(2-N'-methylpiperazinoethyl)hydrazone from
B and 2-N'-methylpiperazinoethylhydrazine.

(b)

3. From 3-phenyl-7-chloro-3,4-dihydroacridine-1,9(2H,10H)-dione=D and N-methyl-N'-aminopiperazine, D 1-N-methyl-N'-piperazinimine is obtained 4. From 3-(4-fluorophenyl)-7-chloro-3,4-dihydroacridine-1,9(2H,10H)-dione=E and N-methyl-N'-aminopiperazine, E-1-N-methyl-N'-piperazinimine is obtained.

5. From 3-(2-chlorophenyl)-7-chloro-3,4-dihydroacridine-1,9(2H,10H)-dione=G and N-methyl-N'-aminopiperazine, G-1-N-methyl-N'-piperazinimine is obtained.

6. From 3-(3-chlorophenyl)-7-chloro-3,4-dihydroacridine-1,9(2H,10H)-dione=L and N-methyl-N'-aminopiperazine, L-1-N-methyl-N'-piperazinimine is obtained.

7. From 3-(2,4-dichlorophenyl)-7-chloro-3,4-dihydroacridine-1,9(2H,10H)-dione=M and N-methyl-N'-aminopiperazine, M-1-N-methyl-N'-piperazinimine of melting point 195° is obtained.

8. From 3-(3,4-dichlorophenyl)-7-chloro-3,4-dihydroacridine-1,9(2H,10H)-dione=Q and N-methyl-N'-aminopiperazine, Q-1-N-methyl-N'-piperazinimine is obtained.

9. From 3-(2-trifluoromethylphenyl)-7-chloro-3,4-dihydroacridine-1,9(2H,10H)-dione=T and N-methyl-N'-aminopiperazine, T-1-N-methyl-N'-piperazinimine is obtained.

10. From 3-(2-chloro-4-trifluoromethylphenyl)-7-chloro-10-hydroxy-3,4-dihydroacridine-1,9(2H,10H)-dione=U and N-methyl-N'-aminopiperazine, U-1-N-methyl-N'-piperazinimine of melting point 242° is obtained.

11. From 3-(4-methoxyphenyl)-7-chloro-3,4-dihydroacridine-1,9(2H,10H)-di9one=V and N-methyl-N'-aminopiperazine, V-1-N-methyl-N'-piperazinimine is obtained.

12. From 3-(4-nitrophenyl)-7-chloro-3,4-dihydroacridine-1,9(2H,10H)-dione=W and N-methyl-N'-aminopiperazine, W-1-N-methyl-N'-piperazinimine is obtained.

(d)

1. From 3-(4-trifluoromethylphenyl)-7-chloro-3,4-dihydroacridine-1,9(2H,10H)-dione=A and aminoguanidine, A-1-guanylhydrazone HCl of melting point 257° is obtained;
A-1-(1,1-dimethyl)semicarbazone from
A and 1,1-dimethylsemicarbazide;
A-1-(1,1-dimethyl)thiosemicarbazone from
A and 1,1-dimethylthiosemicarbazide;
A-1-(1,1-dimethyl)guanylhydrazone from
A and 1,1-dimethylaminoguanidine;
A-1-(N'-methylpiperazino-N-carbonyl)hydrazone from
A and N-hydrazinocarbonyl-N'-methylpiperazine;
A-1-(N'-methylpiperazino-N-thiocarbonyl)hydrazone from
A and N-hydrazinothiocarbonyl-N'-methylpiperazine; and
A-1-(N'-methylpiperazino-N-carbimido)hydrazone from
A and N-hydrazinocarbimido-N'-methylpiperazine.

(e)

1. A-1-[1-(2-N,N-dimethylaminoethyl)]semicarbazone from
A and 1-(2-N,N-dimethylaminoethyl)semicarbazide;
A-1-[1-(2-N,N-diethylaminoethyl)]semicarbazone from
A and 1-(2-N,N-diethylaminoethyl)semicarbazide;
A-1-[1-(2-N-methylpiperazinoethyl)]semicarbazone from
A and 1-(2-N-methylpiperazinoethyl)semicarbazide;
A-1-[1-(2-N,N-dimethylaminoethyl)]thiosemicarbazone from
A and 1-(2-N,N-dimethylaminoethyl)thiosemicarbazide;
A-1-[1-(2-N,N-diethylaminoethyl)]thiosemicarbazone from
A and 1-(2-N,N-diethylaminoethyl)thiosemicarbazide;
A-1-[1-(2-N-methylpiperazinoethyl)]thiosemicarbazone from
A and 1-(2-N-methylpiperazinoethyl)thiosemicarbazide;
A-1-[1-(2-N,N-dimethylaminoethyl)]guanylhydrazone from
A and 1-(2-N,N-dimethylaminoethyl)aminoguanidine;
A-1-[1-(2-N,N-diethylaminoethyl)]guanylhydrazone from
A 1-(2-N,N-diethylaminoethyl)aminoguanidine; and
A-1-[1-(2-N-methylpiperazinoethyl)]guanylhydrazone from
A and 1-(2-N-methylpiperazinoethyl)aminoguanidine.

(d)

2. From 3-(4-chlorophenyl)-7-chloro-3,4-dihydroacridine-1,9(2H,10H)-dione=B and aminoguanidine, B-1-guanylhydrazone.HCL of melting point 270° is obtained
B-1-(1,1-dimethyl)semicarbazone from
B and 1,1-dimethylsemicarbazide;
B-1-(1,1-dimethyl)thiosemicarbazone from
B and 1,1-dimethylthiosemicarbazide;
B-1-(1,1-dimethyl)guanylhydrazone from
B and 1,1-dimethylaminoguanidine;
B-1-(N'-methylpiperazino-N-carbonyl)hydrazone from
B and N-hydrazinocarbonyl-N'-methylpiperazine;

B-1-(N'-methylpiperazino-N-thiocarbonyl)hydrazone from
B and N-hydrazinothiocarbonyl-N'-methylpiperazine; and
B-1-(N'-methylpiperazino-N-thiocarbimido)hydrazone from
B and N-hydrazinothiocarbimido-N'-methylpiperazine.

(e)
2. B-1-[1-(2-N,N-dimethylaminoethyl)]semicarbazone from
B and 1-(2-dimethylaminoethyl)semicarbazide;
B-1-[1-(2-N,N-diethylaminoethyl)]semicarbazone from
B and 1-(2-N,N-diethylaminoethyl)semicarbazide;
B-1-[1-(2-N-methylpiperazinoethyl)]semicarbazone from
B and 1-(2-N-methylpiperazinoethyl)semicarbazide;
B-1-[1-(2-N,N-dimethylaminoethyl)]thiosemicarbazone from
B and 1-(2-N,N-dimethylaminoethyl)thiosemicarbazide;
B-1-[1-(2-N,N-diethylaminoethyl)]thiosemicarbazone from
B and 1-(2-N,N-diethylaminoethyl)thiosemicarbazide;
B-1-[1-(2-N-methylpiperazinoethyl)]thiosemicarbazone from
B and 1-(2-N-methylpiperazinoethyl)thiosemicarbazide;
B-1-[1-(2-N,N-dimethylaminoethyl)]guanylhydrazone from
B and 1-(2-N,N-dimethylaminoethyl)aminoguanidine;
B-1-[1-(2-N,N-diethylaminoethyl)]guanylhydrazone from
B and 1-(2-N,N-diethylaminoethyl)aminoguanidine; and
B-1-[1-(2-N-methylpiperazinoethyl)]guanylhydrazone from
B and 1-(2-N-methylpiperazinoethyl)aminoguanidine.

(f)
1. From 3-(4-trifluoromethylphenyl)-7-chloro-3,4-dihydroacridine-1,9(2H,10H)-dione=A and dimethylaminoacetic acid hydrazide, A-1-(N,N-dimethylaminoacetyl)hydrazone is obtained;
A-1-(N,N-diethylaminoacetyl)hydrazone from
A and N,N-diethylaminoacetic acid hydrazide;
A-1-(N-morpholinoacetyl)hydrazone from
A and morpholinoacetic acid hydrazide;
A-1-(N-methyl-N'-piperazinoacetyl)hydrazone from
A and N-methyl-N'-piperazinoacetic acid hydrazide;
A-1-(2-N,N-dimethylaminopropionyl)hydrazone from
A and 2-N,N-dimethylaminopropionic acid hydrazide;
A-1-(2-N,N-diethylaminopropionyl)hydrazone from
A and 2-N,N-diethylaminopropionic acid hydrazide;
A-1-(2-morpholinopropionyl)hydrazone from
A and 2-morpholinopropionic acid hydrazide;
A-1-(2-N-methyl-N'-piperazinopropionyl)hydrazone from
A and 2-N-methyl-N'-piperazinopropionic acid hydrazide; and
A-1-(N,N,N-trimethylammonioacetyl)hydrazone chloride of melting point 296° from
A and N,N,N-trimethylammonioacetic acid hydrazide chloride.

(g)
1. From 3-(4-trifluoromethylphenyl)-7-chloro-3,4-dihydroacridine-1,9(2H,10H)-dione=A and 2-N,N-dimethylaminoethyl hydrazinoformate, A-1-(2-N,N-dimethylaminoethyloxycarbonyl)hydrazone is obtained;
A-1-(2-N,N-diethylaminoethyloxycarbonyl)hydrazone HCl from
A and 2-N,N-diethylaminoethyl hydrazinoformate;
A-1-(2-morpholinoethyloxycarbonyl)hydrazone from
A and 2-morpholinoethyl hydrazinoformate; and
A-1-(2-N-methyl-N'-piperazinoethyloxycarbonyl)hydrazone from
A and 2-N-methyl-N'-piperazinoethyl hydrazinoformate.

(f)
2. From 3-(4-chlorophenyl)-7-chloro-3,4-dihydroacridine-1,9(2H,10H)-dione=B and dimethylaminoacetic acid hydrazide, B-1-(N,N-dimethylaminoacetyl)hydrazone is obtained;
B-1-(N,N-diethylaminoacetyl)hydrazone from
B and N,N-diethylaminoacetic acid hydrazide;
B-1-(morpholinoacetyl)hydrazone from
B and morpholinoacetic acid hydrazide;
B-1-(N-methyl-N'-piperazinoacetyl)hydrazone from
B and N-methyl-N'-piperazinoacetic acid hydrazide;
B-1-(2-N,N-dimethylaminopropionyl)hydrazone from
B and 2-N,N-dimethylaminopropionic acid hydrazide;
B-1-(2-N,N-diethylaminopropionyl)hydrazone from
B and 2-N,N-diethylaminopropionic acid hydrazide;
B-1-(2-morpholinopropionyl)hydrazone from
B and 2-morpholinopropionic acid hydrazide;
B-1-(2-N-methyl-N'-piperazinopropionyl)hydrazone from
B and 2-N-methyl-N'-piperazinopropionic acid hydrazide; and
B-1-(N,N,N-trimethylammonioacetyl)hydrazone chloride of melting point 280° from
B and N,N,N-trimethylammonioacetic acid hydrazide chloride.

(g)
2. From 3-(4-trifluoromethylphenyl)-7-chloro-3,4-dihydroacridine-1,9(2H,10H)-dione=B and 2-N,N-dimethylaminoethyl hydrazinoformate, B-1-(2-N,N-dimethylaminoethyloxycarbonyl)hydrazone is prepared;
B-1-(2-N,N-diethylaminoethyloxycarbonyl)hydrazone from
B and 2-N,N-diethylaminoethyl hydrazinoformate;
B-1-(2-morpholinoethyloxycarbonyl)hydrazone from
B and 2-morpholinoethyl hydrazinoformate; and
B-1-(2-N-methyl-N'-piperazinoethyloxycarbonyl)hydrazone from
B and 2-N-methyl-N'-piperazinoethyl hydrazinoformate.

We claim:
1. 3-Aryl-7-chloro-3,4-dihydroacridine-1,9(2H,10H)-dione 1-oximes and 1-hydrazone compounds of the formula I

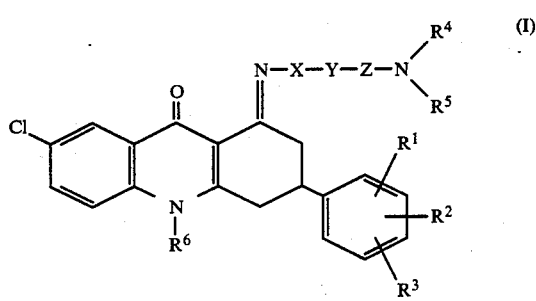

in which $R^1$ denotes hydrogen, halogen, $C_1$–$C_4$-alkyl, trifluoromethyl, $C_1$–$C_4$-alkoxy, trifluoromethoxy, difluorochloromethoxy, 1,1,2,2-tetrafluoroethoxy, phenoxy, halogenophenoxy, $C_1$–$C_4$-alkylthio, phenylthio, naphthylthio, $C_1$–$C_4$-alkylsulfinyl, phenylsulfinyl, naphthylsulfinyl, $C_1$–$C_4$-alkylsulfonyl, phenylsulfonyl, naphthylsulfonyl, trifluoromethylthio, carbamyl, sulfamyl, cyano or nitro, $R^2$ represents hydrogen or halogen, $R^3$ represents hydrogen, (a) X denotes oxygen,
  Y denotes a single bond and
  Z denotes a straight-chain or branched alkylene chain having 2 to 5 carbon atoms which may be substituted with a hydroxy group, or (b) X, Y and Z denote a single bond, or (c) X denotes the —NR— group, in which R denotes hydrogen or $C_1$–$C_4$-alkyl,
  Y denotes a single bond and
  Z denotes a straight-chain or branched alkylene chain having 2 to 5 carbon atoms, or (d) X denotes the —NR— group, in which R denotes hydrogen or $C_1$–$C_4$-alkyl,
  Y denotes the carbonyl, thiocarbonyl or iminocarbonyl group and
  Z denotes a single bond, or (e) X denotes the —NR— group, in which R denotes hydrogen or $C_1$–$C_4$-alkyl,
  Y denotes the carboxamido, thiocarboxamido or carboxamidino group and
  Z denotes a straight-chain or branched alkylene chain having 2 to 5 carbon atoms, or (f) X denotes the —NR— group, in which R denotes hydrogen or $C_1$–$C_4$-alkyl,
  Y denotes the carbonyl group and
  Z denotes a straight-chain or branched alkylene chain having 1 to 3 carbon atoms, or (g) X denotes the —NR— group, in which R denotes hydrogen or $C_1$–$C_4$-alkyl,
  Y denotes the carboxyl group and
  Z denotes a straight-chain or branched alkylene chain having 2 to 5 carbon atoms, and $R^4$ and $R^5$ together with the nitrogen atom, denote a piperazine ring which is unsubstituted on the nitrogen or substituted on the nitrogen by an alkyl group having 1 to 3 carbon atoms which may be substituted by a hydroxyl group, or by phenyl-$C_1$–$C_3$-alkyl or naphthyl-$C_1$–$C_3$-alkyl or by phenyl or naphthyl, which may be substituted by methyl, methoxy, chlorine or trifluoromethyl, and $R^6$ denotes hydrogen or the hydroxyl group, their physiologically tolerated acid addition salts and their physiologically tolerated addition salts of ($C_1$–$C_4$)-alkyl or benzyl halides.

2. 3-Aryl-7-chloro-3,4-dihydroacridine-1,9(2H,10H)-dione 1-oximes and 1-hydrazone compounds of the formula I

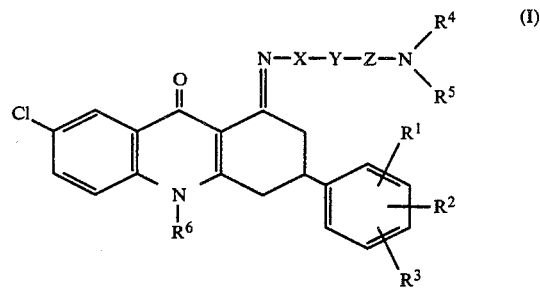

in which $R^1$ denotes chlorine or trifluoromethyl, $R^2$ and $R^3$ represent hydrogen, X and Y and Z denote a single bond and $R^4$ and $R^5$ together with the nitrogen atom, denote a piperazine ring which is unsubstituted on the nitrogen or substituted on the nitrogen by an alkyl group having 1 to 3 carbon atoms which may be substituted by a hydroxy group, or by phenyl-$C_1$–$C_3$-alkyl or naphthyl-$C_1$–$C_3$-alkyl or by phenyl or naphthyl, which may be substituted by methyl, methoxy, chlorine or trifluoromethyl, and $R^6$ denotes hydrogen or the hydroxyl group, their physiologically tolerated acid addition salts and their physiologically tolerated addition salts of ($C_1$–$C_4$)-alkyl or benzyl halides.

3. 3-(4-Trifluoromethylphenyl)-7-chloro-3,4-dihydroacridine-1,9(2H,10H)-dione 1-(N-methyl-N'-piperazinyl)-imine.

4. 3-(4-Trifluoromethylphenyl)-7-chloro-3,4-dihydroacridine-1,9(2H,10H)-dione 1-N-2-hydroxyethyl-N'-piperazinimine.

5. 3-(4-Chlorophenyl)-7-chloro-3,4-dihydroacridine-1,9(2H,10H)-dione 1-N-methyl-N'-piperazinimine.

6. 3-(4-Chlorophenyl)-7-chloro-3,4-dihydroacridine-1,9(2H,10H)-dione 1-N-2-hydroxyethyl-N'-piperazinimine.

7. A pharmaceutical product for use against plasmodia and/or coccidia containing a pharmaceutically effective amount of a compound as claimed in claim 1 and a pharmaceutically acceptable carrier.

8. A method for combating plasmodia and/or coccidia comprising the step of administering a chemotherapeutically effective amount of a compound as claimed in claim 1 to a patient.

* * * * *

UNITED STATES PATENT AND TRADEMARK OFFICE
CERTIFICATE OF CORRECTION

PATENT NO. : 4,593,027

DATED : June 3, 1986

INVENTOR(S) : Erhardt WINKELMANN et al.

It is certified that error appears in the above-identified patent and that said Letters Patent is hereby corrected as shown below:

On the title page:

Line 2, change "Winklemann et al." to --Winkelmann et al.--;

In item [75] Inventors, change "Winklemann" to

--Winkelmann--.

Signed and Sealed this

Tenth Day of March, 1987

Attest:

DONALD J. QUIGG

Attesting Officer

Commissioner of Patents and Trademarks